United States Patent [19]
Adermann et al.

[11] Patent Number: 6,030,790
[45] Date of Patent: Feb. 29, 2000

[54] ANTIBODIES THAT BIND PEPTIDES FROM THE HPTH SEQUENCE (1-37)

[75] Inventors: Knut Adermann, Hannover; Dieter Hock, Neckarbischofsheim; Markus Mägerlein, Obernburg, all of Germany

[73] Assignee: Haemopep Pharma GmbH, Germany

[21] Appl. No.: 08/817,547

[22] PCT Filed: Sep. 22, 1995

[86] PCT No.: PCT/EP95/03757

§ 371 Date: Mar. 27, 1997

§ 102(e) Date: Mar. 27, 1997

[87] PCT Pub. No.: WO96/10041

PCT Pub. Date: Apr. 4, 1996

[30] Foreign Application Priority Data

Sep. 28, 1994 [DE] Germany ............... P 44 34 551

[51] Int. Cl.$^7$ ............... G01N 33/43; C07K 16/26
[52] U.S. Cl. ............ 435/7.1; 436/512; 530/387.1; 530/387.2; 530/387.9; 530/388.24
[58] Field of Search ............ 435/7.1; 436/512; 530/387.1, 387.2, 387.9, 388.24

[56] References Cited

U.S. PATENT DOCUMENTS 4,508,828  4/1985  Lindall et al. ............ 436/500

OTHER PUBLICATIONS

Nussbaum et al. Chemical Abstracts 96(5), Abstract No. 29060, 1982.
Tampe et al. J. Immunoassay 13(1):1–13, 1992.
Daniel et al. Virology 202: 540–549, 1994.
Bowie et al. Science 247:1306–1310, 1990.
Ngo et al. The Protein Folding Problem and Tertiary Structure Prediction, Merz et al., eds., Birkhauser, Boston, pp. 492–495, 1994.

*Primary Examiner*—Elizabeth Kemmerer
*Attorney, Agent, or Firm*—Jones & Askew, LLP

[57] ABSTRACT

The present invention is directed to peptides from the sequence of hPTH(1–37), which contain α-helical amino acid sequence regions and/or non-structured amino acid sequence regions, said peptides being capable of inducing antibodies when injected into animals. Furthermore, the invention is directed to a diagnostic agent and antibodies obtainable by immunizing animals using the peptides according to the invention.

25 Claims, No Drawings

ANTIBODIES THAT BIND PEPTIDES FROM THE HPTH SEQUENCE (1-37)

This application was filed under 35 U.S.C. § 371 and claims priority from PCT/EP95/03757, filed Sep. 22, 1995.

The present invention relates to peptides from the sequence of hPTH(1–37), and the use of said peptides in the preparation of an agent for diagnosing biologically active hPTH.

Human parathyroid hormone (hPTH), a linear polypeptide having 84 amino acids, plays an important role in the regulation of the calcium metabolism. The metabolism of this hormone gives rise to a large number of C-terminal fragments, the biological functions of which have not yet been elucidated. The hPTH(1–37) has been established as a circulating N-terminal fragment (EP-A 0 349 545). This fragment has the full biological activity of the entire hormone. However, upon loss of the first amino acid, serine, the activity significantly decreases and is lost completely without the first two amino acids, serine and valine.

Serum levels in the range of $10^{-12}$ mol/l are measured for the intact hormone hPTH(1–84) and for the N-terminal fragment. Immunological measuring procedures are employed to determine such low concentrations. Here, the most valid results are provided by measuring procedures according to the double antibody or sandwich principle (e.g., the two-site radioimmunometric assay, IRMA, or the sandwich enzyme-linked immuno sorbent assay, Sandwich ELISA). For hPTH(1–84), such assays are commercially available. For the measurement of hPTH(1–34), an assay according to the double antibody principle is not known.

Here, two antibodies are required. In order to avoid mutual steric hindrance, they must be capable of recognizing antigen epitopes located at a sufficient distance from each other. When immunizing using the intact antigen, a heterogeneous mixture of various antibodies is obtained, which first must be subjected to an expensive purification in order to conduct a sandwich assay. According to theoretical calculations by B. A. Jameson and H. Wolf, The Antigenic Index: A Novel Algorithm for Predicting Antigenic Determinants, CABIOS 4, p. 181–186, 1988; it has been possible so far to detect a preferred sequence having immunogenic activity in the region of the amino acids 7–14 at the N-terminus. Immunization with N-terminal fragments according to established methods predominantly results in antibodies which, as has been described for hPTH(1–34) (J. Tampe, P. Brozio, H. E. Manneck, A. Miβbichler, E. Blind, K. B. Millers, H. SchmidtGayk, and F. P. Armbruster, Characterisation of Antibodies Against Human N-Terminal Parathyroid Hormone by Epitope Mapping; J. Immunoassay 13, p. 1–13, 1992), bind in the region of these amino acids. However, these antibodies are not capable of discriminating between biologically active and biologically inactive PTH (1–84) or fragments thereof lacking the first two amino acids serine and valine.

The technical problem which this invention is based upon is to provide peptides by means of which it is possible to eliminate the above-mentioned drawbacks in the diagnosis of biologically active hPTH.

Surprisingly, the technical problem described above is solved by means of the following peptides from the sequence of hPTH(1–37):

```
hPTH 1-10 SEQ I.D. NO.1
NH2-Ser1-Val2-Ser3-Glu4-Ile5-Gln6-Leu7-Met8-His9-Asn10-OH                          (1)

hPTH 1-9 SEQ I.D. NO.2
NH2-Ser1-Val2-Ser3-Glu4-Ile5-Gln6-Leu7-Met8-His9-OH                                (2)

hPTH 1-8 SEQ I.D. NO.3
NH2-Ser1-Val2-Ser3-Glu4-Ile5-Gln6-Leu7-Met8-OH                                     (3)

hPTH 1-7 SEQ I.D. NO.4
NH2-Ser1-Val2-Ser3-Glu4-Ile5-Gln6-Leu7-OH                                          (4)

hPTH 1-6 SEQ I.D. NO.5
NH2-Ser1-Val2-Ser3-Glu4-Ile5-Gln6-OH                                               (5)

hPTH 1-5 SEQ I.D. NO.6
NH2-Ser1-Val2-Ser3-Glu4-Ile5-OH                                                    (6)

hPTH 9-18 SEQ I.D. NO.7
NH2-His9-Asn10-Leu11-Gly12-Lys13-His14-Leu15-Asn16-Ser17-Met18-OH                  (7)

hPTH 10-18 SEQ I.D. NO.8
NH2-Asn10-Leu11-Gly12-Lys13-His14-Leu15-Asn16-Ser17-Met18-OH                       (8)

hPTH 11-18 SEQ I.D. NO.9
NH2-Leu11-Gly12-Lys13-His14-Leu15-Asn16-Ser17-Met18-OH                             (9)

hPTH 12-18 SEQ I.D. NO.10
NH2-Gly12-Lys13-His14-Leu15-Asn16-Ser17-Met18-OH                                  (10)

hPTH 13-18 SEQ I.D. NO.11
NH2-Lys13-His14-Leu15-Asn16-Ser17-Met18-OH                                        (11)

hPTH 14-18 SEQ I.D. NO.12
NH2-His14-Leu15-Asn16-Ser17-Met18-OH                                              (12)

hPTH 9-17 SEQ I.D. NO.13
NH2-His9-Asn10-Leu11-Gly12-Lys13-His14-Leu15-Asn16-Ser17-OH                       (13)

hPTH 9-16 SEQ I.D. NO.14
```

-continued hPTH 9-16 (continued)
NH$_2$-His$^9$-Asn$^{10}$-Leu$^{11}$-Gly$^{12}$-Lys$^{13}$-His$^{14}$-Leu$^{15}$-Asn$^{16}$-OH  (14)

hPTH 9-15 SEQ I.D. NO.15
NH$_2$-His$^9$-Asn$^{10}$-Leu$^{11}$-Gly$^{12}$-Lys$^{13}$-His$^{14}$-Leu$^{15}$-OH  (15)

hPTH 9-14 SEQ I.D. NO.16
NH$_2$-His$^9$-Asn$^{10}$-Leu$^{11}$-Gly$^{12}$-Lys$^{13}$-His$^{14}$-OH  (16)

hPTH 9-13 SEQ I.D. NO.17
NH$_2$-His$^9$-Asn$^{10}$-Leu$^{11}$-Gly$^{12}$-Lys$^{13}$-OH  (17)

hPTH 24-37 SEQ I.D. NO.18
NH$_2$-Leu$^{24}$-Arg$^{25}$-Lys$^{26}$-Lys$^{27}$-Leu$^{28}$-Gln$^{29}$-Asp$^{30}$-Val$^{31}$-His$^{32}$-Asn$^{33}$-
Phe$^{34}$-Val$^{35}$-Ala$^{36}$-Leu$^{37}$-OH  (18)

hPTH 25-37 SEQ I.D. NO.19
NH$_2$-Arg$^{25}$-Lys$^{26}$-Lys$^{27}$-Leu$^{28}$-Gln$^{29}$-Asp$^{30}$-Val$^{31}$-His$^{32}$-Asn$^{33}$-
Phe$^{34}$-Val$^{35}$-Ala$^{36}$-Leu$^{37}$-OH  (19)

hPTH 26-37 SEQ I.D. NO.20
NH$_2$-Lys$^{26}$-Lys$^{27}$-Leu$^{28}$-Gln$^{29}$-Asp$^{30}$-Val$^{31}$-His$^{32}$-Asn$^{33}$-
Phe$^{34}$-Val$^{35}$-Ala$^{36}$-Leu$^{37}$-OH  (20)

hPTH 27-37 SEQ I.D. NO.21
NH$_2$-Lys$^{27}$-Leu$^{28}$-Gln$^{29}$-Asp$^{30}$-Val$^{31}$-His$^{32}$-Asn$^{33}$-
Phe$^{34}$-Val$^{35}$-Ala$^{36}$-Leu$^{37}$-OH  (21)

hPTH 28-37 SEQ I.D. NO.22
NH$_2$-Leu$^{28}$-Gln$^{29}$-Asp$^{30}$-Val$^{31}$-His$^{32}$-Asn$^{33}$-Phe$^{34}$-Val$^{35}$-Ala$^{36}$-Leu$^{37}$-OH  (22)

hPTH 29-37 SEQ I.D. NO.23
NH$_2$-Gln$^{29}$-Asp$^{30}$-Val$^{31}$-His$^{32}$-Asn$^{33}$-Phe$^{34}$-Val$^{35}$-Ala$^{36}$-Leu$^{37}$-OH  (23)

hPTH 30-37 SEQ I.D. NO.24
NH$_2$-Asp$^{30}$-Val$^{31}$-His$^{32}$-Asn$^{33}$-Phe$^{34}$-Val$^{35}$-Ala$^{36}$-Leu$^{37}$-OH  (24)

hPTH 31-37 SEQ I.D. NO.25
NH$_2$-Val$^{31}$-His$^{32}$-Asn$^{33}$-Phe$^{34}$-Val$^{35}$-Ala$^{36}$-Leu$^{37}$-OH  (25)

hPTH 32-37 SEQ I.D. NO.26
NH$_2$-His$^{32}$-Asn$^{33}$-Phe$^{34}$-Val$^{35}$-Ala$^{36}$-Leu$^{37}$-OH  (26)

hPTH 33-37 SEQ I.D. NO.27
NH$_2$-Asn$^{33}$-Phe$^{34}$-Val$^{35}$-Ala$^{36}$-Leu$^{37}$-OH  (27)

hPTH 24-36 SEQ I.D. NO.28
NH$_2$-Leu$^{24}$-Arg$^{25}$-Lys$^{26}$-Lys$^{27}$-Leu$^{28}$-Gln$^{29}$-Asp$^{30}$-Val$^{31}$-His$^{32}$-Asn$^{33}$-
Phe$^{34}$-Val$^{35}$-Ala$^{36}$-OH  (28)

hPTH 24-35 SEQ I.D. NO.29
NH$_2$-Leu$^{24}$-Arg$^{25}$-Lys$^{26}$-Lys$^{27}$-Leu$^{28}$-Gln$^{29}$-Asp$^{30}$-Val$^{31}$-His$^{32}$-Asn$^{33}$-
Phe$^{34}$-Val$^{35}$-OH  (29)

hPTH 24-34 SEQ I.D. NO.30
NH$_2$-Leu$^{24}$-Arg$^{25}$-Lys$^{26}$-Lys$^{27}$-Leu$^{28}$-Gln$^{29}$-Asp$^{30}$-Val$^{31}$-His$^{32}$-Asn$^{33}$-
Phe$^{34}$-OH  (30)

hPTH 24-33 SEQ I.D. NO.31
NH$_2$-Leu$^{24}$-Arg$^{25}$-Lys$^{26}$-Lys$^{27}$-Leu$^{28}$-Gln$^{29}$-Asp$^{30}$-Val$^{31}$-His$^{32}$-Asn$^{33}$-OH  (31)

hPTH 24-32 SEQ I.D. NO.32
NH$_2$-Leu$^{24}$-Arg$^{25}$-Lys$^{26}$-Lys$^{27}$-Leu$^{28}$-Gln$^{29}$-Asp$^{30}$-Val$^{31}$-His$^{32}$-OH  (32)

hPTH 24-31 SEQ I.D. NO.33
NH$_2$-Leu$^{24}$-Arg$^{25}$-Lys$^{26}$-Lys$^{27}$-Leu$^{28}$-Gln$^{29}$-Asp$^{30}$-Val$^{31}$-OH  (33)

hPTH 24-29 SEQ I.D. NO.34
NH$_2$-Leu$^{24}$-Arg$^{25}$-Lys$^{26}$-Lys$^{27}$-Leu$^{28}$-Gln$^{29}$-OH  (34)

hPTH 24-38 SEQ I.D. NO.35
NH$_2$-Leu$^{24}$-Arg$^{25}$-Lys$^{26}$-Lys$^{27}$-Leu$^{28}$-OH  (35)

The indicated sequences represent essential features of the secondary structure in their primary structure, as can be demonstrated by supporting NMR data. One precondition to this end was a determination of the PTH(1–37) secondary structure in physiological solution.

The above-mentioned regions of conspicuous structure have good immunogenic activity. Antibodies are formed, binding to the first amino acids of the N-terminus. Deficiency of only two amino acids gives rise to a substantial loss in affinity. Because these amino acids are indispensable for the biological activity to arise, it is possible by using the peptides of the invention to obtain antibodies recognizing only hPTH and fragments thereof which are biologically active.

Furthermore, antibodies can be produced which detect the mid-region 9–15, as well as antibodies giving C-terminal binding in the region of the amino acids 30–37. According to the invention, it is therefore possible to produce antibodies against hPTH(1–37) regions which, according to theoretical calculations, do not exhibit immunogenic activity within the entire molecule. In addition, these regions are separated from each other by such a far distance that no steric hindrance is present which would prevent simultaneous binding of two antibodies.

In preferred embodiments, the peptides may be modified at the N-terminal end, in the side-chain and/or at the C-terminal end, namely, taking the form of acetylation, amidation, phosphorylation and/or glycosylation products.

Eventually, the peptides of the invention may also be bound to carrier proteins such as hemocyanin, thyroglobulin, bovine serum albumin, ovalbumin, or mouse serum albumin etc. Binding to the carrier proteins is preferably effected using carbodiimide or formaldehyde.

The peptides of the invention may be used in the preparation of a diagnostic agent. The diagnostic agent of the invention can be obtained using the per se known immunization of animals with at least one of the peptides according to the invention. Following immunization, an immunoglobulin fraction can be isolated from the immunized animals, which contains antibody fractions having an antibody titer against at least one of the peptides of the invention. The invention is also directed to the antibodies thus obtained. In addition to the complete antibodies consisting of $F_{ab}$ and $F_c$, fragments thereof such as $F_{ab}$ or fragments of the antibodies being idiotypes of peptide epitopes may also be used in an alternative embodiment.

The peptides according to the invention are suitable for preparing an agent for the diagnosis of biologically active hPTH(1–37).

Referring to the following examples, the invention will be described in more detail.

EXAMPLE 1
Solid-Phase Synthesis of Peptides

The method of the invention for synthesizing the peptides is based on the peptide synthesis using a solid support. Each of the C-terminal amino acids is bound to the support material in the presence of dicyclohexylcarbodiimide and dimethylaminopyridine. Wang resin or similar resins are used as support material for the syntheses.

The following derivatives of L-amino acids are used in the synthesis of the sequence, starting from the peptidyl resin as specified: a) hPTH(1–10) Seq. I.D. No. 1: Fmoc-Asn(Trt)-Wang resin, Fmoc-His(Trt)-OH, Fmoc-Met-OH, Fmoc-Leu-OH, Fmoc-Gln(Trt)-OH, Fmoc-Ile-OH, Fmoc-Glu(OtBu)-OH, Fmoc-Ser(tBu)-OH, Fmoc-Val-OH, Boc-Ser(tBu)-OH; b) hPTH(9–18) Seq. I.D. No. 7: Fmoc-Met-Wang resin, Fmoc-Ser(tBu)-OH, Fmoc-Asn(Trt)-OH, Fmoc-Leu-OH, Fmoc-His(Trt)-OH, Fmoc-Lys(Boc)-OH, Fmoc-Gly-OH, Fmoc-Leu-OH, Fmoc-Asn(Trt)-OH, Boc-His(Trt)-OH; c) hPTH(24–37) Seq. I.D. No. 18: Fmoc-Leu-Wang resin, Fmoc-Ala-OH, Fmoc-Val-OH, Fmoc-Phe-OH, Fmoc-Asn(Trt)-OH, Fmoc-His(Trt)-OH, Fmoc-Val-OH, Fmoc-Asp(OtBu)-OH, Fmoc-Gln(Trt)-OH, Fmoc-Leu-OH, Fmoc-Lys(Boc)-OH, Fmoc-Lys(Boc)-OH, Fmoc-Arg(Pmc)-OH, Fmoc-Leu-OH.

The synthesis may be carried out by in situ activation using 2-(1H-benzotriazol-1-yl)-1,1,3,3-tetramethyluronium tetrafluoroborate (TBTU) or derivatives thereof, or benzotriazol-1-yloxy-tris(dimethylamino)phosphonium hexafluorophosphate (BOP) or derivatives thereof in the presence of diisopropylethylamine or N-methylmorpholine and 1-hydroxybenzotriazole, using a four- to tenfold excess of Fmoc-L-amino acid during the coupling reactions in N,N-dimethylformamide, N,N-dimethylacetamide or N-methylpyrrolidone. Removal of the Fmoc groups is effected using 20% piperidine or 2% piperidine and 2% 1,8-diazabicyclo[5.4.0]undec-7-ene (DBU) in N,N-dimethylformamide, N,N-dimethylacetamide or N-methylpyrrolidone. Following synthesis, the resins are washed with 2-propanol and dichloromethane and dried to constant weight in a high vacuum.

Removal from the support and deprotection are carried out by reacting the peptidyl resin with trifluoroacetic acid containing 5% scavenger, water, ethanediol, phenol or thioanisole for 30–90 minutes at room temperature, filtrating, washing with trifluoroacetic acid, and subsequently precipitating with tert-butyl methyl ether. The precipitate is lyophilized from aqueous solution.

EXAMPLE 2
Purification and Analysis

The raw products are purified by chromatography on a C18 reversed phase column (10 μm, buffer A: 0.01 N HCl in water; buffer B: 20% isopropanol, 30% methanol, 50% water, 0.01 N HCl; gradient: 10–80% within 60 minutes; detection at 230 nm).

The purity of the products is determined using mass spectrometry and C18 reversed phase chromatography.

EXAMPLE 3
Coupling to Carrier Protein

Used as carrier proteins are hemocyanin, thyroglobulin, bovine serum albumin, ovalbumin, or mouse serum albumin. Coupling is performed according to the carbodiimide method by way of the carboxyl groups of the peptides. The peptide is activated in aqueous solution by reaction with 1-ethyl-3-(3-methylaminopropyl)carbodiimide hydrochloride for 5 minutes. Coupling is effected by adding the activated peptide to an aqueous solution of the carrier. The molar ratio is 1 peptide 50 amino acids of the carrier protein. The reaction takes 4 hours.

We claim:

1. A kit for detecting active human parathyroid hormone (hPTH) comprising a container and a first group of antibodies or antibody fragments and a second group of antibodies or antibody fragments, wherein the first group selectively binds a peptide of hPTH selected from the group consisting of peptides having SEQ. ID. Nos. 1–6 and the second group selectively binds hPTH at an epitope contained within amino acids 24 to 37.

2. The kit of claim 1, wherein the second group of antibodies or antibody fragments selectively binds a peptide of hPTH selected from the group consisting of peptides having SEQ. ID. Nos. 18–36.

3. The kit of claim 1, wherein the first group of antibodies or antibody fragments selectively bind peptides of hPTH having SEQ. ID. No. 1.

4. The kit of claim 1, wherein the first group of antibodies or antibody fragments selectively bind peptides of hPTH having SEQ. ID. No. 2.

5. The kit of claim 1, wherein the first group of antibodies or antibody fragments selectively bind peptides of hPTH having SEQ. ID. No. 3.

6. The kit of claim 1, wherein the first group of antibodies or antibody fragments selectively bind peptides of hPTH having SEQ. ID. No. 4.

7. The kit of claim 1, wherein the first group of antibodies or antibody fragments selectively bind peptides of hPTH having SEQ. ID. No. 5.

8. The kit of claim 1, wherein the first group of antibodies or antibody fragments selectively bind peptides of hPTH having SEQ. ID. No. 6.

9. An immunological method of detecting active human parathyroid hormone (hPTH) in a sample comprising:

contacting the sample with a first antibody or antibody fragment which selectively binds a peptide of hPTH selected from the group consisting of peptides having SEQ. ID. Nos. 1–6, wherein the first antibody or antibody fragment binds hPTH in the sample;

contacting the sample with a second antibody or antibody fragment which selectively binds hPTH at an epitope contained within amino acids 24 to 37; wherein the second antibody or antibody fragment binds to hPTH bound by the first antibody or antibody fragment; and detecting the binding of the first and second antibodies or antibody fragments, wherein the binding of the first and second antibodies or antibody fragments indicates the presence of active hPTH in the sample.

10. The method of claim 9, wherein the second antibody or antibody fragment selectively binds a peptide of hPTH selected from the group consisting of peptides having SEQ. ID. Nos. 18–36.

11. The method of claim 9, wherein the first antibody or antibody fragment selectively binds peptides of hPTH having SEQ. ID. No. 1.

12. The method of claim 9, wherein the first antibody or antibody fragment selectively binds peptides of hPTH having SEQ. ID. No. 2.

13. The method of claim 9, wherein the first antibody or antibody fragment selectively binds peptides of hPTH having SEQ. ID. No. 3.

14. The method of claim 9, wherein the first antibody or antibody fragment selectively binds peptides of hPTH having SEQ. ID. No. 4.

15. The method of claim 9, wherein the first antibody or antibody fragment selectively binds peptides of hPTH having SEQ. ID. No. 5.

16. The method of claim 9, wherein the first antibody or antibody fragment selectively binds peptides of hPTH having SEQ. ID. No. 6.

17. A composition comprising an antibody or antibody fragment and a suitable carrier, wherein the antibody or antibody fragment selectively binds a peptide of human parathyroid hormone (hPTH) selected from the group consisting of peptides having SEQ. ID. Nos. 1–6.

18. The composition of claim 17, wherein the composition further comprises a second antibody or antibody fragment, wherein the second antibody or antibody fragment selectively binds hPTH at an epitope contained within amino acids 24 to 37.

19. The composition of claim 17, wherein the second antibody or antibody fragment selectively binds a peptide of hPTH selected from the group consisting of peptides having SEQ. ID. Nos. 18–36.

20. The composition of claim 17, wherein the antibody or antibody fragment selectively binds peptides of hPTH having SEQ. ID. No. 1.

21. The composition of claim 17, wherein the antibody or antibody fragment selectively binds peptides of hPTH having SEQ. ID. No. 2.

22. The composition of claim 17, wherein the antibody or antibody fragment selectively binds peptides of hPTH having SEQ. ID. No. 3.

23. The composition of claim 17, wherein the antibody or antibody fragment selectively binds peptides of hPTH having SEQ. ID. No. 4.

24. The composition of claim 17, wherein the antibody or antibody fragment selectively binds peptides pf hPTH having SEQ. ID. No. 5.

25. The composition of claim 17, wherein the antibody or antibody fragment selectivley binds peptides of hPTH having SEQ. ID. No. 6.

* * * * *

UNITED STATES PATENT AND TRADEMARK OFFICE
Certificate

Patent No. 6,030,790                          Patented: February 29, 2000

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Wolf-Georg Forssmann, Hanover, Germany; Knut Adermann, Hanover, Germany; Dieter Hock, Neckarbischofsheim, Germany; and Markus Mägerlein, Obernburg, Germany.

Signed and Sealed this Sixth Day of August 2002.

YVONNE EYLER, Ph. D.
*Supervisory Patent Examiner*
Art Unit 1646

UNITED STATES PATENT AND TRADEMARK OFFICE
CERTIFICATE OF CORRECTION

PATENT NO.    : 6,030,790
DATED         : March 27, 1997
INVENTOR(S)   : Knut Andermann et al.

It is certified that error appears in the above-identified patent and that said Letters Patent is hereby corrected as shown below:

Column 6,
After line 56, insert the following text:
-- The reaction is stopped by adding sodium acetate with a final concentration of 100mM. Incubation is allowed to proceed for one hour.

The protein-peptide conjugate is seperated from the peptide by repeated dialysis against 100mM phosphatebuffer,pH 7.2.

Example 4
Synthesis of the Multiple Antigenic Peptides (MAP)

The triple lysine branching is achieved by binding Fmoc-L-lysine (Fmoc) -OH to C-terminal alanine bound to Wang resin using three coupling cyles. Cleavage with piperidine then results in eight free amino functions where the sequences of the human parathyroid hormone are synthesized according to the above description.

Example 5
Immunization

For the first immunization, 125 mg of carrier-peptide conjugate or MAP per kg body weight of the animal to be immunized is dissolved in 250 ml of water and emulsified with 250 ml of complete Freund adjuvant. The emulsion is applied subcutaneously in 10 portions at various positions on the back.

Boosting is carried out after 2-4 weeks in an analogous fashion, the only change being the substitution of the complete Freund adjuvant by the incomplete Freund adjuvant.--

Signed and Sealed this

Twenty-seventh Day of August, 2002

*Attest:*

*Attesting Officer*

JAMES E. ROGAN
*Director of the United States Patent and Trademark Office*

(12) EX PARTE REEXAMINATION CERTIFICATE (7166th)
United States Patent
Adermann et al.

(10) Number: US 6,030,790 C1
(45) Certificate Issued: Nov. 17, 2009

(54) ANTIBODIES THAT BIND PEPTIDES FROM THE HPTH SEQUENCE (1-37)

(75) Inventors: Knut Adermann, Hannover (DE); Dieter Hock, Neckarbischofsheim (DE); Markus Mägerlein, Obernburg (DE)

(73) Assignee: Pharis Biotec GmbH, Hannover (DE)

Reexamination Request:
No. 90/007,412, Feb. 4, 2005

Reexamination Certificate for:
Patent No.: 6,030,790
Issued: Feb. 29, 2000
Appl. No.: 08/817,547
Filed: Mar. 27, 1997

Certificate of Correction issued Aug. 27, 2002.

(22) PCT Filed: Sep. 22, 1995

(86) PCT No.: PCT/EP95/03757
§ 371 (c)(1),
(2), (4) Date: Mar. 27, 1997

(87) PCT Pub. No.: WO96/10041
PCT Pub. Date: Apr. 4, 1996

(30) Foreign Application Priority Data

Sep. 28, 1994 (DE) .......................................... P4434551

(51) Int. Cl.
*A61K 39/00* (2006.01)
*C07K 14/435* (2006.01)
*C07K 14/635* (2006.01)

(52) U.S. Cl. ...................... 435/7.1; 436/512; 530/387.1; 530/387.2; 530/387.9; 530/388.24

(58) Field of Classification Search ........................ None
See application file for complete search history.

(56) References Cited

U.S. PATENT DOCUMENTS 4,469,787 A * 9/1984 Woods et al. ................. 435/7.4
4,788,138 A * 11/1988 Tung et al. ....................... 435/5
5,744,444 A * 4/1998 Forssmann et al. ............ 514/12

FOREIGN PATENT DOCUMENTS

WO    WO 91/06564       5/1991
WO    WO 9403201 A1 *   2/1994

OTHER PUBLICATIONS

Magerlein, M., et al. Immunological Detection of Human Parathyroid Hormone 1–37 (hPTH 1–37), the Physiologically Circulating Fragment of hPTH. European Journal of Pharmaceutical Sciences, 2 (1994), pt. 1/2, p. 254.*
Harlow, E. et al. Antibodies, 1988, pp. 366, 428, 584, and 579.*
Adermann, K., et al., "Aspects of Synthesis and Analysis of Multiple Antigen Peptides," *Innovations and Perspectives in Solid Phase Synthesis,* Mayflower Worldwide, Birmingham, United Kingdom, pp. 429–432 (1994).

Cruse, J.M., et al., *Illustrated Dictionary of Immunology,* Second Edition, CRC Press, Boca Raton, pp. 37 and 56 (2002).
Fischer, J.A., et al., "Immunological Characterization of Antibodies Against a Glandular Extract and the Synthetic Amino–terminalFragments 1–12 and 1–34 and their use in the Determination of Immunoreactive Hormone in Human Sera", *J. Clin. Invest.* vol.l 54, pp. 1382–1394 (1974).
Harlow, E. (Editor), "Immunoaffinity Purification of Antibodies on an Antigen Column," *Antibodies,* (Adapted from Campbell et al., 1951) Cold Spring Harbor Laboratory, pp. 313–315 (1988).
Harlow, E. (Editor), "Immunoaffinity Purification of Antibodies on an Antigen Column," *Antibodies,* (Adapted from Campbell et al., 1951) Cold Spring Harbor Laboratory, pp. 288–295 (1988).
Harlow, E. (Editor), "Immunoaffinity Purification of Antibodies on an Antigen Column," *Antibodies,* (Adapted from Campbell et al., 1951) Cold Spring Harbor Laboratory, pp. 579–581 (1988).
Lackie, J.M., et al., Dictionary of Cell and Molecular Biology, Third Edition, University of Glasgow, Academic Press, London, p. 364.
LePage R., et al., "A non–(1–84) circulating parathyroid hormone (PTH) fragment interferes significantly with intact PTH commercial assay measurements in uremic samples", Clinical Chemistry, vol. 44, No. 4, pp. 805–809 (1998).
Logue, F.C., et al., "Production and characterization of monoclonal antibodies to parathyroid hormone (1–34)", *J. Immunol. Meth.,* vol. 137, pp. 159–166 (1991).
Magerlein, M. et al., "A New Immunoenzymometric Assay for Bioactive N–Terminal Human Parthyroid Hormone Fragments and Its Application in Pharmacokinetic Studies in Dogs," *Arzneimittel–Forschung/Drug Research,* vol. 48, No. 1, Germany, pp. 199–204 (1998).
Magerlein, M., et al., "Immunological Detection of Human Parathyroid Hormone 1–37 (hPTH 1–37) the Physiologically Circulating Fragment of hPTH," *Eur. J. of Sciences,* vol. 2, pp. 117–194 (1994).
Magerlein, M., et al., "Production of Sequence Specific Polyclonal Antibodies to Human Parathyroid Hormone 1–37 by Immunization with Multiple Antigenic Peptides," *Arzneimittel–Forschung/Drug Research,* vol. 48, No. 2, Germany, pp. 783–787 (1998).
Mapping, E., "Characterization of Antibodies Against Human N–Terminal Parathyroid Hormone," *J. of Immunoassay,* vol. 13, No. 1, pp. 1–13 (1992).

(Continued)

*Primary Examiner*—Brenda Brumback

(57) ABSTRACT

The present invention is directed to peptides from the sequence of hPTH(1-37), which contain α-helical amino acid sequence regions and/or non-structured amino acid sequence regions, said peptides being capable of inducing antibodies when injected into animals. Furthermore, the invention is directed to a diagnostic agent and antibodies obtainable by immunizing animals using the peptides according to the invention.

OTHER PUBLICATIONS

*Nichols Institute Diagnostics, Inc. v. Scantibodies Clinical Lab., Inc.,* In the United States District Court Southern District of California, Civil Action No. 02–CV–0046B (LAB), Deposition of Knut Adermann, pp. 22–25, 51–52, 141–142 (2003).

*Nichols Institute Diagnostics, Inc. v. Scantibodies clinical Lab., Inc.,* In the United States District Court Southern District of California, Civil Action No. 02–CV–0046B (JMA), Order Denying Defendants' Motion for Summary Judgement of Invalidity of United States patent No. 6,030,790 and Granting Summary Adjudication that the Patent is not Anticipated or Rendered Obvious by Certain Prior Art References (2003).

*Nichols Institute Diagnostics, Inc. v. Scantibodies Clinical Lab., Inc.,* In the United States District Court Southern District of California, Civil Action No. 02–CV–0046B (LAB), Declaration of Andrew William Smith in Support of Motion for Summary Judgment Pursuant to 35 USC 102(b) by Defendants Scantibodies Clinical Laboratory, Inc. and Scantibodies Laboratory, Inc. (2002).

*Nichols Institute Diagnostics, Inc. v. Scantibodies Clinical Lab., Inc.,* In the United States District Court Southern District of California, Civil Action No. 02–CV–0046B (LAB), Order Denying defendants' Motion for Summary Judgment and Granting Summary Adjudication, pp. 1–5 (2003).

*Nichols Institute Diagnostics, Inc. v. Scantibodies Clinical Lab., Inc.,* In the United States District Court Southern District of California, Civil Action No. 02–CV–0046B (LAB), Declaration of Kimberly L. Briggs in Support of Motion for Summary Judgment Pursuant to 35 USC 102(b) by Defendants Scantibodies Clinical Laboratory, Inc. and Scantibodies Laboratory, Inc. (2002).

*Nichols Institute Diagnostics, Inc. v. Scantibodies Clinical Lab., Inc.,* In the United States District Court Southern District of California, Civil Action No. 02–CV–0046B (LAB), Declaration of Marianne Kranenborg in Support of Motion for Summary Judgment Pursuant to 35 USC 102(b) by Defendants Scantibodies Clinical Laboratory, Inc. and Scantibodies Laboratory, Inc. (2003).

*Nichols Institute Diagnostics, Inc. v. Scantibodies Clinical Lab., Inc.,* In the United States District Court Southern District of California, Civil Action No. 02–CV–0046B (LAB), Order Construing Patent Claims and Terms for Jury Trial, pp. 1–14 (2003).

*Nichols Institute Diagnostics, Inc. v. Scantibodies Clinical Lab., Inc.,* In the United States District Court Southern District of California, Civil Action No. 02–CV–0046B (LAB), Rebuttal Expert Report of Claude Arnaud, M.D., FACE, pp. 1–11 (2004).

*Nichols Institute Diagnostics, Inc. v. Scantibodies Clinical Lab., Inc.,* In the United States District Court Southern District of California, Civil Action No. 02–CV–0046B (LAB), Oral and Videotaped Deposition of Ellen S. Vitetta. Ph.D., pp. 1, 37–38, 62–63, 76–78, 91–93, 159–161, 182, 261–262 (2005).

*Nichols Institute Diagnostics, Inc. v. Scantibodies Clinical Lab., Inc.,* In the United States District Court Southern District of California, Civil Action No. 02–CV–0046B (LAB), Transcript of Motion Hearing Before the Honorable Rudi M. Brewster U.S.D.C. Judge, pp. 1, 70, 91 (2005).

*Nichols Institute Diagnostics, Inc. v. Scantibodies Clinical Lab., Inc.,* In the United States District Court Southern District of California, Civil Action No. 02–CV–0046B (LAB), Transcript of Motion Hearing Before the Honorable Rudi M. Brewster U.S.D.C. Judge, pp. i, ii, 1–55 (2005).

*Nichols Institute Diagnostics, Inc. v. Scantibodies Clinical Lab., Inc.,* In the United States District Court Southern District of California, Civil Action No. 02–CV–0046B (LAB), Transcript of Tutorial Hearing Before the Honorable Rudi M. Brewster U.S.D.C. Judge, pp. 1,ii, 39, 247 (2002).

*Nichols Institute Diagnostics, Inc. v. Scantibodies Clinical Lab., Inc.,* In the United States District Court Southern District of California, Civil Action No. 02–CV–0046B (LAB), Declaration of Dr. Leonard J. Deftos in Support of Plaintiff Nichols Institute Diagnostics Inc.'s Second Supplemental Claim Construction Brief, pp. i, 1–10 (2003).

Tam, J.P. "Synthetic Peptide Vaccine Design: Synthesis and Properties of a High–Density Multiple Antigenic Peptide System", *Proc Natl Acad Sci. USA,* vol. 85, pp. 5409–5413 (1988).

Tampe, J., et al., "Characterization of antibodies Against Human N–Terminal Parathyroid Hormone by Epitope Mapping," *J. of Immunogassay,* vol. 13, No. 1,pp. 1–14 (1992).

* cited by examiner

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–25 are cancelled.

\* \* \* \* \*

SEQUENCE LISTING (1) GENERAL INFORMATION:

(iii) NUMBER OF SEQUENCES: 36

```
(2) INFORMATION FOR SEQ ID NO: 1:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 1:

Ser Val Ser Glu Ile Gln Leu Met His Asn
1               5                   10

(2) INFORMATION FOR SEQ ID NO: 2:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 2:

Ser Val Ser Glu Ile Gln Leu Met His
1               5

(2) INFORMATION FOR SEQ ID NO: 3:

(i) SEQUENCE CHARACTERISTICS:
        (A) LENGTH: 8 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 3:

Ser Val Ser Glu Ile Gln Leu Met
1               5

(2) INFORMATION FOR SEQ ID NO: 4:

(i) SEQUENCE CHARACTERISTICS:
        (A) LENGTH: 7 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 4:

Ser Val Ser Glu Ile Gln Leu
1               5
```

(2) INFORMATION FOR SEQ ID NO: 5:

(i) SEQUENCE CHARACTERISTICS:
        (A) LENGTH: 6 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 5:

Ser Val Ser Glu Ile Gln
1               5

(2) INFORMATION FOR SEQ ID NO: 6:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 6:

Ser Val Ser Glu Ile
1               5

(2) INFORMATION FOR SEQ ID NO: 7:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 7:

His Asn Leu Gly Lys His Leu Asn Ser Met
1               5                   10

(2) INFORMATION FOR SEQ ID NO: 8:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 8:

Asn Leu Gly Lys His Leu Asn Ser Met
1               5

(2) INFORMATION FOR SEQ ID NO: 9:

(i) SEQUENCE CHARACTERISTICS:
        (A) LENGTH: 8 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 9:

Leu Gly Lys His Leu Asn Ser Met
1               5

(2) INFORMATION FOR SEQ ID NO: 10:

(i) SEQUENCE CHARACTERISTICS:
        (A) LENGTH: 7 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 10:

Gly Lys His Leu Asn Ser Met
1               5

(2) INFORMATION FOR SEQ ID NO: 11:

(i) SEQUENCE CHARACTERISTICS:
        (A) LENGTH: 6 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 11:

Lys His Leu Asn Ser Met
1               5

(2) INFORMATION FOR SEQ ID NO: 12:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 12:

His Leu Asn Ser Met

```
1               5

(2) INFORMATION FOR SEQ ID NO: 13:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 13:

His Asn Leu Gly Lys His Leu Asn Ser
1               5

(2) INFORMATION FOR SEQ ID NO: 14:

(i) SEQUENCE CHARACTERISTICS:
        (A) LENGTH: 8 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 14:

His Asn Leu Gly Lys His Leu Asn
1               5

(2) INFORMATION FOR SEQ ID NO: 15:

(i) SEQUENCE CHARACTERISTICS:
        (A) LENGTH: 7 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 15:

His Asn Leu Gly Lys His Leu
1               5

(2) INFORMATION FOR SEQ ID NO: 16:

(i) SEQUENCE CHARACTERISTICS:
        (A) LENGTH: 6 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 16:
```

```
His Asn Leu Gly Lys His
1               5

(2) INFORMATION FOR SEQ ID NO: 17:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 17:

His Asn Leu Gly Lys
1               5

(2) INFORMATION FOR SEQ ID NO: 18:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 18:

Leu Arg Lys Lys Leu Gln Asp Val His Asn Phe Val Ala Leu
1               5                   10

(2) INFORMATION FOR SEQ ID NO: 19:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 19:

Arg Lys Lys Leu Gln Asp Val His Asn Phe Val Ala Leu
1               5                   10

(2) INFORMATION FOR SEQ ID NO: 20:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 20:
```

```
Lys Lys Leu Gln Asp Val His Asn Phe Val Ala Leu
1               5                   10
```

(2) INFORMATION FOR SEQ ID NO: 21:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 21:

```
Lys Leu Gln Asp Val His Asn Phe Val Ala Leu
1               5                   10
```

(2) INFORMATION FOR SEQ ID NO: 22:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 22:

```
Leu Gln Asp Val His Asn Phe Val Ala Leu
1               5                   10
```

(2) INFORMATION FOR SEQ ID NO: 23:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 23:

```
Gln Asp Val His Asn Phe Val Ala Leu
1               5
```

(2) INFORMATION FOR SEQ ID NO: 24:

(i) SEQUENCE CHARACTERISTICS:
        (A) LENGTH: 8 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 24:

Asp Val His Asn Phe Val Ala Leu
1               5

(2) INFORMATION FOR SEQ ID NO: 25:

(i) SEQUENCE CHARACTERISTICS:
        (A) LENGTH: 7 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 25:

Val His Asn Phe Val Ala Leu
1               5

(2) INFORMATION FOR SEQ ID NO: 26:

(i) SEQUENCE CHARACTERISTICS:
        (A) LENGTH: 6 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 26:

His Asn Phe Val Ala Leu
1               5

(2) INFORMATION FOR SEQ ID NO: 27:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 27:

Asn Phe Val Ala Leu
1               5

(2) INFORMATION FOR SEQ ID NO: 28:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 28:

Leu Arg Lys Lys Leu Gln Asp Val His Asn Phe Val Ala
1               5                   10

(2) INFORMATION FOR SEQ ID NO: 29:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 29:

Leu Arg Lys Lys Leu Gln Asp Val His Asn Phe Val
1               5                   10

(2) INFORMATION FOR SEQ ID NO: 30:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 30:

Leu Arg Lys Lys Leu Gln Asp Val His Asn Phe
1               5                   10

(2) INFORMATION FOR SEQ ID NO: 31:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 31:

Leu Arg Lys Lys Leu Gln Asp Val His Asn
1               5                   10

(2) INFORMATION FOR SEQ ID NO: 32:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 32:

Leu Arg Lys Lys Leu Gln Asp Val His
1               5

(2) INFORMATION FOR SEQ ID NO: 33:

(i) SEQUENCE CHARACTERISTICS:
        (A) LENGTH: 8 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 33:

Leu Arg Lys Lys Leu Gln Asp Val
1               5

(2) INFORMATION FOR SEQ ID NO: 34:

(i) SEQUENCE CHARACTERISTICS:
        (A) LENGTH: 7 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 34:

Leu Arg Lys Lys Leu Gln Asp
1               5

(2) INFORMATION FOR SEQ ID NO: 35:

(i) SEQUENCE CHARACTERISTICS:
        (A) LENGTH: 6 amino acids
        (B) TYPE: amino acid
        (C) STRANDEDNESS: unknown
        (D) TOPOLOGY: unknown (ii) MOLECULE TYPE: peptide (iii) HYPOTHETICAL: no (iv) ANTI-SENSE: no (xi) SEQUENCE DESCRIPTION: SEQ ID NO: 35:

Leu Arg Lys Lys Leu Gln
1               5

(2) INFORMATION FOR SEQ ID NO: 36:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (ii) MOLECULE TYPE: peptide (iii) HYPOTHETICAL: no -continued (iv) ANTI-SENSE: no (xi) SEQUENCE DESCRIPTION: SEQ ID NO: 36:

Leu Arg Lys Lys Leu
1               5